(12) United States Patent
Tang et al.

(10) Patent No.: US 8,258,187 B2
(45) Date of Patent: *Sep. 4, 2012

(54) MATERIALS AND METHODS FOR IMPROVING ALCOHOL METABOLISM AND ALLEVIATING THE EFFECTS OF HANGOVERS

(75) Inventors: Wen Qin Tang, Shanghai (CN); Francis Chi, Kowloon (HK)

(73) Assignee: Omega Bio-Pharma (I.P.1) Ltd., Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 12/890,890

(22) Filed: Sep. 27, 2010

(65) Prior Publication Data

US 2011/0015275 A1    Jan. 20, 2011

Related U.S. Application Data

(63) Continuation of application No. 10/982,160, filed on Nov. 5, 2004, now Pat. No. 7,803,843.

(60) Provisional application No. 60/523,451, filed on Nov. 19, 2003.

(51) Int. Cl.
*A01N 33/08* (2006.01)
*A61K 31/13* (2006.01)

(52) U.S. Cl. .......................... 514/665; 514/642; 514/579

(58) Field of Classification Search ........................ None
See application file for complete search history.

(56) References Cited

U.S. PATENT DOCUMENTS

| | | | |
|---|---|---|---|
| 4,945,094 A | 7/1990 | Salim | |
| 5,284,874 A | 2/1994 | Clark et al. | |
| 5,401,880 A | 3/1995 | Clark et al. | |
| 5,668,117 A | 9/1997 | Shapiro | |
| 5,714,519 A | 2/1998 | Cincotta et al. | |
| 6,521,266 B1 | 2/2003 | Mann | |
| 6,630,176 B2 | 10/2003 | Li et al. | |
| 6,746,678 B1 | 6/2004 | Shapiro | |
| 7,759,398 B2 | 7/2010 | Chan et al. | |
| 7,803,843 B2* | 9/2010 | Tang et al. | 514/665 |
| 2001/0033881 A1 | 10/2001 | Fuchs et al. | |
| 2004/0033985 A1 | 2/2004 | Chi et al. | |
| 2004/0106591 A1 | 6/2004 | Pacioretty et al. | |
| 2005/0137125 A1 | 6/2005 | Chan et al. | |
| 2005/0143473 A1 | 6/2005 | Wong et al. | |

FOREIGN PATENT DOCUMENTS

| | | |
|---|---|---|
| JP | 2002187839 | 7/2002 |
| WO | WO 8701285 | 3/1987 |
| WO | WO 95/01096 | 1/1995 |
| WO | WO 01/95944 | 12/2001 |

OTHER PUBLICATIONS

Ezer et al., Cysteamine protects against diarrhoea induced by castor oil, this protective effect can be potentiated by SH-alkylator treatment, 1988, Acta Physiologica Hungariea, vol. 71, No. 3, pp. 429-433.*

Dupre, S. et al., "The Enzymatic Breakdown of Pantethine to Pantothenic Acid and Cystamine," *Eur. J. Biochem.*, 1970, pp. 571-578, vol. 16.

Gyenes, L. et al., "The Properties of Fragments of Skin-Sensitizing and Blocking Antibodies as Revealed by the Prausnitz-Kuestner, Passive Cutaneous Anaphylaxis and Hemagglutination Reactions," *International Archives of Allergy and Applied Immunology*, 1964, pp. 106-118, vol. 24.

Kano, M. et al., "Soymilk Products Affect Ethanol Absorption and Metabolism in Rats During Acute and Chronic Ethanol Intake," *American Society for Nutritional Sciences*, 2002, pp. 238-244.

Landers, M.C. et al., "Permanent-Wave Dermatitis: Contact Allergy to Cysteamine Hydrochloride," *American Journal of Contact Dermatitis*, 2003, pp. 157-160, vol. 14, No. 3.

McCarty, M.F., "Inhibition of acetyl-CoA caboxylase by cystamine may mediate the hypotriglyceridemic activity of pantethine," *Medical Hypotheses*, 2001, pp. 314-317, vol. 56, No. 3.

Stahl et al., "*Handbook of Pharmaceutical Salts: Properties, Selection, and Use*," 2002, Wiley-VCH, pp. 1-7.

Vescei et al., "Preclinical and Clinical Studies With Cysteamine and Pantethine Related to the Central Nervous System," *Prg. Neuropsychopharmacol.*, 1990, pp. 835-862, vol. 14.

Wall, T.L. et al., "Alcohol Metabolism in Asian American Men With Genetic Polymorphisms of Aldehyde Dehydrogenase," *Annals of Int. Med.*, 1997, pp. 376-379, vol. 127, No. 5.

Watanabe et al., "Activation and Inhibition of Yeast Aldehyde Dehydrogenase Activity by Pantethine and its Metabolites," *Ann. Nutr. Metab.*, 1986, pp. 54-57, vol. 30.

Watanabe et al., "Alcoholism: Clinical and Experimental Research," 1985, pp. 272, vol. 9, Issue 3, abstract only.

Windholz et al., The Merck Index, Tenth Edition, 1983, pp. 849-850, Abstract No. 5792.

Wittwer et al., "Metabolism of Pantethine in cystinosis," *The Journal of Clinical Investigation, Inc.*, 1985, pp. 1665-1672, vol. 76.

* cited by examiner

*Primary Examiner* — Jeffrey S. Lundgren

*Assistant Examiner* — Meghan Finn

(74) *Attorney, Agent, or Firm* — Saliwanchik, Lloyd & Eisenschenk

(57) ABSTRACT

The subject invention provides materials and methods for improving alcohol metabolism in animals. In a preferred embodiment, the invention provides methods for increasing the ability of people to consume alcohol while reducing hangovers or other effects of intoxication. Specifically exemplified herein is the use of a cysteamine compound to reduce the adverse effects of alcohol consumption. For example, the undesirable and unpleasant symptoms association with hangovers can be reduced through consumption, according to the subject invention, of cysteamine hydrochloride.

11 Claims, 4 Drawing Sheets

MATERIALS AND METHODS FOR IMPROVING ALCOHOL METABOLISM AND ALLEVIATING THE EFFECTS OF HANGOVERS

CROSS-REFERENCE TO A RELATED APPLICATION

This application is a continuation of application Ser. No. 10/982,160, filed Nov. 5, 2004; now U.S. Pat. No. 7,803,843 which claims the benefit of provisional patent application Ser. No. 60/523,451, filed Nov. 19, 2003, both of which are hereby incorporated by reference in their entirety.

BACKGROUND OF INVENTION

Metabolism is the body's process of converting ingested substances to other compounds. Metabolism involves a number of processes, one of which is referred to as oxidation. Through oxidation, alcohol is detoxified and removed from the blood, preventing the alcohol from accumulating and harming cells and organs. Until all the alcohol consumed has been metabolized, it is distributed throughout the body, affecting the brain, liver, and other tissues and organs.

When alcohol is consumed, it is absorbed into the blood from the stomach and intestines. Alcohol is then metabolized through the action of enzymes. Specifically, in the liver, alcohol dehydrogenase (ADH) mediates the conversion of alcohol to acetaldehyde.

Acetaldehyde is then quantitatively oxidized to acetic acid in the presence of aldehyde dehydrogenase (ALDH) and nicotinamide-adenine dinucleotide (NAD).

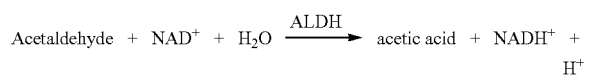

$$\text{Acetaldehyde} + \text{NAD}^+ + \text{H}_2\text{O} \xrightarrow{\text{ALDH}} \text{acetic acid} + \text{NADH}^+ + \text{H}^+$$

Acetate is eventually metabolized to carbon dioxide and water.

Alcohol also is metabolized in the liver by cytochrome P450IIE1 (CYP2E1), which may be increased after chronic drinking.

The microsomol ethanol oxidizing system (MEOS) is also involved in alcohol metabolism. Ethanol induces MEOS activity while lowering ALDH activity (Lebsack, M. E., E. R. Gordon, and C. S. Lieber, 1981 "Effect of chronic ethanol consumption on aldehyde dehydrogenase activity in the baboon" *Biochem. Pharmacol.* 30:2273-2277); therefore, acetaldehyde and reactive oxygen species accumulate upon chronic or high consumption of ethanol. These toxic molecules can cause cell injury through lipid peroxidation, protein inactivation and DNA damage.

The liver can metabolize only a certain amount of alcohol per hour. The rate of alcohol metabolism depends, in part, on the amount of metabolizing enzymes in the liver, which varies among individuals and has genetic determinants. In general, after the consumption of one standard drink, the amount of alcohol in the drinker's blood (blood alcohol concentration, or BAC) peaks within 30 to 45 minutes. Alcohol is metabolized more slowly than it is absorbed. Since the metabolism of alcohol is slow, alcohol can accumulate in the body and intoxication occurs.

A number of factors influence the process of alcohol absorption, including the presence of food and the type of food in the gastrointestinal tract when alcohol is consumed.

The rate at which alcohol is absorbed depends on how quickly the stomach empties its contents into the intestine. For example, the higher the dietary fat content, the more time this emptying will require and the longer the process of absorption will take.

Thus, dietary components can affect ethanol absorption and metabolism. Ethanol absorption is controlled mainly by gastric emptying, because the primary region of ethanol absorption is the small intestine. Vegetable oils such as soybean oil and coconut oil delay the elimination rate of gastric ethanol and lessen the increase in plasma ethanol concentration. Moreover, because ethanol-metabolizing enzymes such as ADH, ALDH and MEOS contribute to the clearance of ethanol and toxic acetaldehyde, components that stimulate these enzyme activities are expected to ameliorate alcohol toxicity. For example, sesamin and garlic stimulate ethanol metabolism, especially acetaldehyde clearance (Yang, Z, Y. Suwa, K. Hirai et al. 1995, "Effects of sesamin on ethanol-induced muscle relaxation" *J. Jpn. Soc. Nutr. Food Sci.* 48:103-108; and Kishimoto, R., M. Ueda, H. Yoshinaga, K. Goda, S.-S. Park (1999) "Combined effects of ethanol and garlic on hepatic ethanol metabolism in mice" *J. Nutr. Sci. Vitaminol.* 45:275-286).

There are also differences in alcohol metabolism based on gender. Women absorb and metabolize alcohol differently from men. Women tend to have higher BAC's after consuming the same amount of alcohol as men and are more susceptible to alcoholic liver disease, heart muscle damage, and brain damage. The difference in BAC's between women and men has been attributed to women's smaller amount of body water. An additional factor contributing to the difference in BAC's may be that women have lower activity of the alcohol metabolizing enzyme ADH in the stomach, causing a larger proportion of the ingested alcohol to reach the blood.

Alcohol consumption and metabolism can have very important health consequences. For example, although moderate doses of alcohol added to the diets of lean men and women do not seem to lead to weight gain, some studies have reported weight gain when alcohol is added to the diets of overweight persons.

Also, alcohol metabolism alters the balance of reproductive hormones in men and women. In men, alcohol metabolism contributes to testicular injury and impairs testosterone synthesis and sperm production. Prolonged testosterone deficiency may contribute to feminization in males, for example, breast enlargement.

In women, alcohol metabolism may contribute to increased production of a form of estrogen called estradiol (which contributes to increased bone density and reduced risk of coronary artery disease) and to decreased estradiol metabolism, resulting in elevated estradiol levels.

Chronic heavy drinking appears to activate the enzyme CYP2E1, which may be responsible for transforming the over-the-counter pain reliever acetaminophen (TYLENOL) into chemicals that can cause liver damage. Alcohol consumption affects the metabolism of a wide variety of other medications, increasing the activity of some and diminishing the activity, thereby decreasing the effectiveness, of others.

In addition to possible life-threatening drug interactions and long-term potential deleterious effects of alcohol intoxication on various organs and systems, alcohol consumption and intoxication can result in short-term, but very unpleasant or inconvenient, effects. These effects, commonly collectively referred to as a "hangover," can include, for example, headaches, nausea, and fatigue. Many hangover "remedies" have been proposed with mixed success. See, for example, U.S. Pat. Nos. 6,221,358 and 6,485,758.

The problems associated with alcohol intoxication and hangovers can be particularly acute for individuals having a genetic variation that reduces their natural ability to metabolize and detoxify alcohol. Asian populations (including, for example Chinese and Japanese) inherit primarily the active ADH2 variant whereby alcohol is rapidly converted to acetaldehyde, but they also primarily inherit the inactive AIDH22 gene whereby the toxic acetaldehyde is not converted to acetate, so it accumulates in the blood. A systemic adverse reaction ensues.

Soybeans are consumed in Japan as part of an ordinary diet. Tofu and "edamame," boiled fresh soybeans, are popular snacks to consume with alcohol, although few reports have been published about the effect of soy products on ethanol consumption. However, isoflavones prepared from the crude extract of Pueraria lobata are used as a traditional medicine for anti-inebriation and suppress alcohol intake by alcohol-preferring rats (Lin, R. C., S. Guthrie, C. Y. Xie et al. 1996 "Isoflavonoid compounds extracted from Pueraria lobata suppress alcohol preference in a pharmacogenetic rat model of alcoholism" Alcohol Clin. Exp. Res. 20:659-663; and Overstreet, D. H., Y. W. Lee, A. H. Rezvani et al. 1996 "Suppression of alcohol intake after administration of the Chinese herbal medicine, NPI-028, and its derivatives" Alcohol Clin. Exp. Res. 20:221-227). The major components of the extract, daidzin and daidzein, are inhibitors in vitro of mitochondrial low $K_m$ ALDH (Keung, W.-M. and B. L. Vallee, 1993, "Daidzin: a potent, selective inhibitor of human mitochondrial aldehyde dehydrogenase" Proc. Natl. Acad. Sci. USA 90:1247-1251) and ADH (W. M. Keung, 1993, "Biochemical studies of a new class of alcohol dehydrogenase inhibitors from Raix puerarae" Alcohol Clin. Exp. Res. 17:1254-1260), whereas intragastric or intraperitoneal injection of daidzin to rodents does not affect these enzyme activities (Keung, W.-M., O. Lazo, L. Kunze, B. L. Vallee, 1995 "Daidzin suppresses ethanol consumption by Syrian golden hamsters without blocking acetaldehyde metabolism" Pro. Natl. Acad. Sci. USA 92:8990-8993; and Xie, C. I., R. C. Lin, V. Antony et al., 1994 "Daidzin, an antioxidant isoflavonoid, decreases blood alcohol levels and shortens sleep time induced by ethanol intoxication" Alcohol Clin. Exp. Res. 18:1443-1447).

Kano et al., who studied the effects of soymilk (SM) products, including fermented soymilk (FSM), on ethanol absorption and metabolism ("Soymilk Products Affect Ethanol Absorption and Metabolism in Rats during Acute and Chronic Ethanol Intake," Kano, M., F. Ishikawa, S. Matsubara, H. Kikuchi-Hayakawa and Y. Shimakawa, Yakult Central Institute for Microbiological Research, Yaho 1796, Kunitachi, Tokyo 186-8650, Japan, J. Nutr. 132:238-244, 2002), found that soy products inhibit ethanol absorption and enhance ethanol metabolism, and that isoflavones may be the active factors. Soy isoflavones have antioxidative activity, acting to reinforce the system. It was also found that soy products improve parameters of cell injury due to chronic ethanol exposure and that soymilk products contribute to the suppression of ethanol-induced cell injury.

Soy products appear to alter ethanol metabolism through inhibition of cytochrome $P_{450}$ (CYP)2E1 in MEOS. Chae et al. (Chae, Y.-H., C. B. Marcus, D. K. Ho et al., 1991, "Effects of synthetic and naturally occurring flavonoids on benzojalpyrene metabolism by hepatic microsomes prepared from rats treated with cytochrome P-450 inducers" Can. Lett. 60:15-24) reported that genistein is a potent inhibitor of CYP1A1 and/or CYP1A2 induced by β-naphthoflavone, and Ronis et al. (Ronis, M. J., J. C. Rowlands, R. Hakkak and T. M. Badger, 1999, "Altered expression and glucocorticoid-inducibility of hepatic CYP3A and CYP2B enzymes in male rats fed diets containing soy protein isolate" J. Nutr. 129: 1958-1965) found that soy protein increases the dexamethasone-induced mRNA expression of hepatic CYP3A2 compared with casein, suggesting a relationship between soy components and the cytochrome $P_{450}$ system, although the effects of soy components on CYP2E1 are not yet known. Thus, the consumption of soy products contributes to the prevention of ethanol-induced liver injury through enhancement of ethanol metabolism and the antioxidation system.

Despite the availability of certain strategies for reducing hangovers, there remains a great need for better approaches to enhance alcohol metabolism and detoxification, especially for certain Asians, and others, who have a reduced ability to metabolize alcohol into non-toxic compounds.

BRIEF SUMMARY

The subject invention provides materials and methods for improving alcohol metabolism in animals. In a preferred embodiment, the invention provides methods for increasing the ability of people to consume alcohol while reducing hangovers or other effects of intoxication.

Specifically exemplified herein is the use of a cysteamine compound to reduce the adverse effects of alcohol consumption. For example, the undesirable and unpleasant symptoms association with hangovers can be reduced through consumption, according to the subject invention, of cysteamine hydrochloride.

Further advantages of the subject invention include effective protection of the liver due to a higher rate of detoxification of alcohol.

A further aspect of the invention is the provision of compositions, which comprise cysteamine hydrochloride, that can be used according to the subject invention to ameliorate the adverse and toxic effects of alcohol consumption.

DETAILED DISCLOSURE

The subject invention provides materials and methods for improving alcohol metabolism and detoxification in animals. In preferred embodiments, the invention provides methods and compositions for increasing the ability of people to consume alcohol while reducing hangovers or other effects of intoxication.

The symptoms of a hangover can include headache, dehydration, congestion, stomach pains, and diarrhea. The hangover is caused by the breakdown of alcohol in the liver especially acetaldehyde which has been found to be highly toxic.

Specifically exemplified herein is the use of cysteamine hydrochloride (and/or analogs, derivatives and prodrugs thereof) to reduce the adverse effects of alcohol consumption.

For example, the undesirable and unpleasant symptoms association with hangovers can be reduced through consumption, according to the subject invention, of a cysteamine compound.

Further advantages of the subject invention include effective protection of the liver due to a higher rate of detoxification of alcohol.

As used herein, reference to a "cysteamine compound" includes the various cysteamine salts (such as cysteamine hydrochloride and cysteamine phosphate) as well as prodrugs of cysteamine that can, for example, be readily metabolized in the body to produce cysteamine. Also included within the scope of the subject invention are analogs of cysteamine which have the ability as described herein to reduce the effects of hangovers and/or increase acetaldehyde dehydrogenase activity. Various analogs, derivatives, conjugates, and metabolites of cysteamine are well known and readily used by those skilled in the art and include, for example, compounds, compositions and methods of delivery as set forth in U.S. Pat. Nos. 6,521,266; 6,468,522; and 5,714,519.

Figure 4:
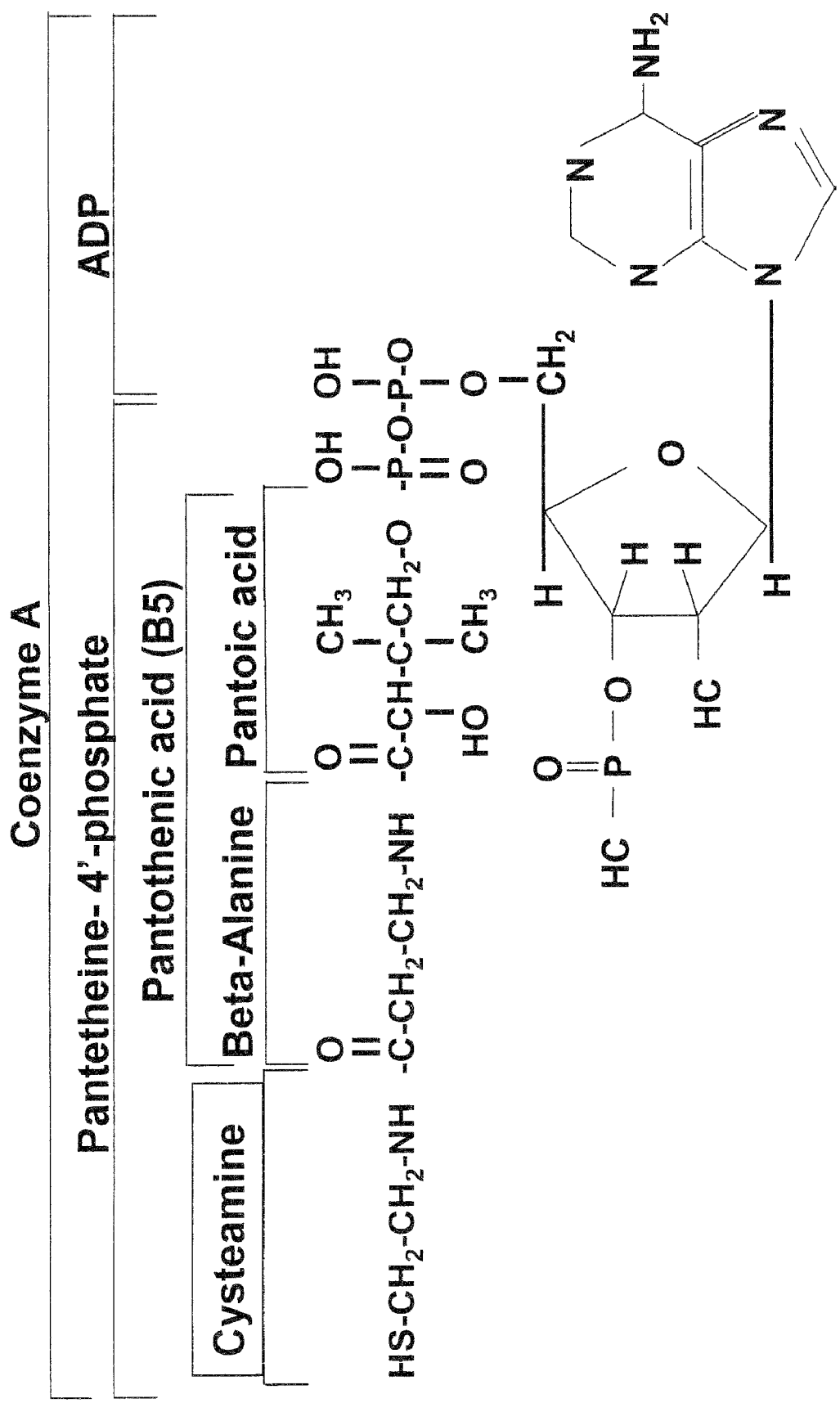
FIG. 4 shows a metabolic pathway of cysteamine.
Figure 5:
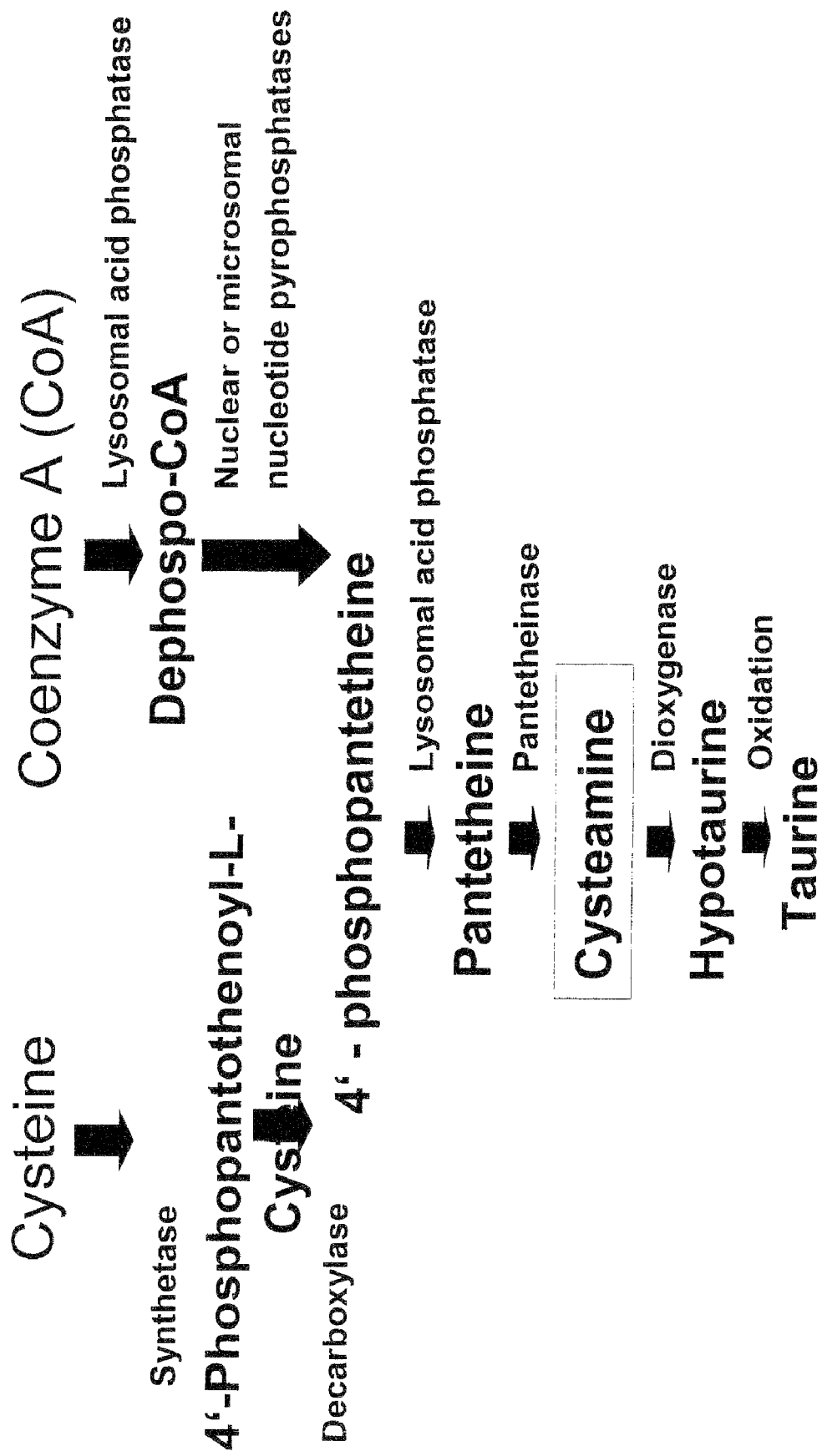
FIG. 5 shows cysteamine as a constituent of co-enzyme A.

In one embodiment of the subject invention, the advantages of cysteamine, as set forth herein, can be achieved by promoting the endogenous production of cysteamine through natural metabolic process such as through the action of co-enzyme A or as a metabolite of cysteine (see FIGS. 4 and 5). This can be achieved by, for example, the administration of pantothenic acid.

One method to increase levels of cysteamine involves pantothenic acid. Pantothenic acid is a naturally occurring vitamin that is converted in mammals to coenzyme A, a substance vital to many physiological reactions. Cysteamine is a component of coenzyme A, and increasing coenzyme A levels results in increased levels of circulating cysteamine. Alkali metal salts, such as magnesium phosphate tribasic and magnesium sulphite (Epsom salts), enhance formation of coenzyme A. Furthermore, breakdown of coenzyme A to cysteamine is enhanced by the presence of a reducing agent, such as citric acid. Thus, the combination of pantothenic acid and alkali metal salts results in increased coenzyme A production and, concomitantly, cysteamine.

In one embodiment, the subject invention provides methods for lowering ethanol concentrations in the plasma of individuals who have consumed alcoholic beverages. This is achieved, at least in part, by increasing alcohol dehydrogenase (ADH) activity in the liver. Thus, individuals who take a cysteamine compound in accordance with the subject invention can improve the ADH activity and, advantageously, lower the plasma concentration of ethanol.

A further advantage obtained through the practice of the subject invention is an increase in acetaldehyde dehydrogenase (ALDH) activity. This, too, helps enhance the metabolism and detoxification of ethanol.

Accordingly, through the practice of the subject invention, the activity of important enzymes can be enhanced, plasma levels of ethanol decreased, and the negative effects of hangovers reduced or eliminated. A further advantage is a decreased risk to the liver and other organs from ethanol and/or toxic intermediate metabolites in the metabolism of ethanol.

Advantageously, the subject invention also provides compositions and methods that can reduce the effects of hangovers and/or speed the time for recovery for an individual after they have ingested large quantities of alcohol. The term "alcohol" as used herein refers to ethyl alcohol and "alcoholic beverages" and refers to spirits or blends that are intended for human consumption. In a preferred embodiment, the cysteamine compound is formulated in a patentable and easily consumed oral formulation such as a pill, lozenge, tablet, gum, beverage, etc. The consumption is then taken at, shortly before, or after, the time of alcohol consumption.

The present application is also directed to a kit having at least one compartment, wherein a first compartment comprises a composition comprising an effective amount of a cysteamine compound of the subject invention. In certain embodiments where the kit has more than one compartment, a second compartment includes at least one item appropriate for an individual who has, or will, consume alcohol.

The additional item, which would typically be separately compartmentalized within the kit, may be either humorous or functional, or both. The additional item may be, for example, an item that will help alleviate hangover effects. Such items include, but are not limited to, analgesics, supplements, food items, compositions to relieve upset stomach, and caffeine. Accordingly, the additional item may be selected from the following: a supplement composition comprising vitamins (such as vitamins B, E, and C) and minerals (such as potassium); a nutritional bar such as a protein bar; a composition comprising acetaminophen; and a composition comprising a stimulant such as caffeine, ephedra, or ma huang.

Examples of humorous items that can be included in a kit of the subject invention include, but are not limited to, items relating to sexual performance (such as VIAGRA (Pfizer), toy handcuffs, etc.); contact information for taxis or other appropriate services; and items useful in promoting sleep (such as earplugs, blindfold, etc.).

In certain embodiments, the composition comprising a cysteamine compound of the invention may be provided in a container (for example, a disposable packet; a bottle with a childproof cap; a cellophane bag, etc.). The kit would also typically contain instructions.

MATERIALS AND METHODS

Experiment Design:
1. Select 30 Wistar male rat (10 weeks old, 300-350 g), divided into 3 groups. Group one is negative control (no ethanol and CT2000 treatment), group two is control (treated with ethanol only); Group three is treatment group (treated with both ethanol and CT2000).
2. 99.9% Ethanol (Analytical Grade) was diluted to 60% for usage.
3. CT2000 can be obtained from Shanghai Walcom Bio-Chem Co. Ltd. which is located at T15-3, Ground Floor, No. 999 Ning Qiao Road, Pudong, Shanghai, China. CT2000 is composed of about 37% cysteamine hydrochloride, while the rest is carrier e.g., starch, microcrystalline cellulose, sodium alignate etc.

Treatment Method:
1. Before the experiment, the rats were left in the cage for 7 days for them to adapt to the environment. Before the ethanol treatment, the rats were not fed for 16 hours overnight. In the next morning at 11:00 am, the negative control and control groups were treated with 1 ml saline per rat, while the treatment group was treated with CT2000 at a dosage of 20 mg/kg body weight.
    One hour later, the negative control was treated with glucose 4.8 g/kg body weight. While the control group and the treatment group were treated with ethanol 2.7 g/kg bw.
2. Sampling: Two hours after administering ethanol, the rats were sacrificed and blood and liver were collected and stored in liquid nitrogen under −70° C.

3. Sample Analysis
   1. Plasma ethanol was measured by F-Kits Ethanol. Ethanol can be readily measured by those skilled in the art using, for example, standard assays such as those available from Boehringer Mannheim (Roche)
   2. Liver alcohol dehydrogenase and acetaldehyde dehydrogenase were measured according to the methods described in "Soymilk Products Affect Ethanol Absorption and Metabolism in Rats during Acute and Chronic Ethanol Intake," Kano, M., F. Ishikawa, S. Matsubara, H. Kikuchi-Hayakawa and Y. Shimakawa, Yakult Central Institute for Microbiological Research, Yaho 1796, Kunitachi, Tokyo 186-8650, Japan, *J. Nutr.* 132:238-244, 2002. The procedures were simplified by normalize the value by the weight of liver instead of the proten level. In addition, the activity measured was expressed as optical density (OD) value without converting into the NADH quantities.

Following are examples which illustrate procedures for practicing the invention. These examples should not be construed as limiting. All percentages are by weight and all solvent mixture proportions are by volume unless otherwise noted.

EXAMPLE 1

Reduction in Plasma Ethanol Level

Figure 1:
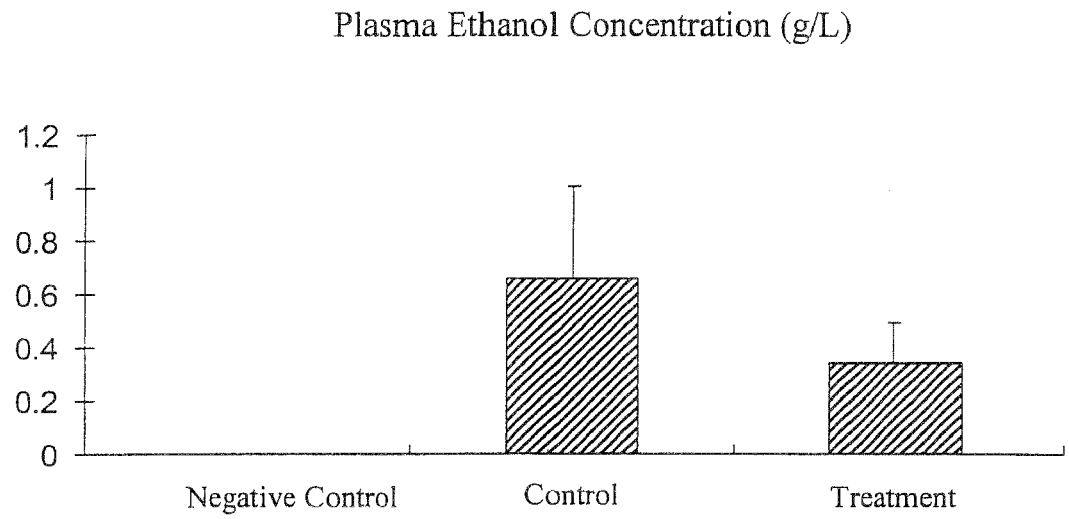
FIG. 1 shows a decrease in plasma ethanol concentration achieved through the practice of the subject invention.

As shown in Table 1 and FIG. 1, use of CT2000 results in a reduction in plasma ethanol levels after ingestion of ethanol.

TABLE 1

|  | Negative Control | Control | Treatment |
|---|---|---|---|
| Average | 0 | 0.66 | 0.34 |
| SD | 0 | 0.34 | 0.15 |

Note:
One tail, Control vs Treatment, n = 6 per group; also, negative control showed negative figures which were regarded as zero.

EXAMPLE 2

Alcohol Dehydrogenase (ADH) Activity in Liver

Figure 2:
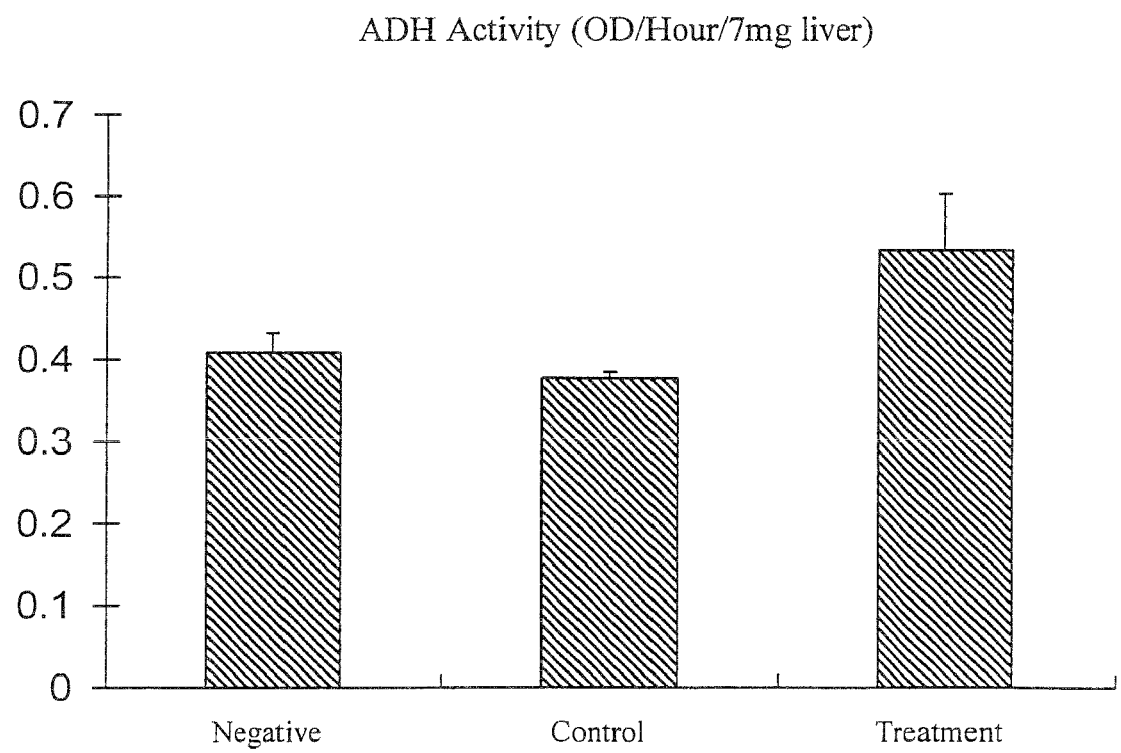
FIG. 2 shows an increase alcohol dehydrogenase (ADH) activity achieved through the practice of the subject invention.

As shown in Table 2 and FIG. 2, use of CT2000 results in an increase in ADH activity after ingestion of ethanol.

TABLE 2

|  | Negative Control | Control | Treatment |
|---|---|---|---|
| Average | 0.1 | 0.38 | 0.53 |
| SD | 0.023 | 0.0075 | 0.068 |

Note:
One tail, Control vs Treatment, n = 6 per group

EXAMPLE 3

Alcohol Acetaldehyde (ALDH) Activity in Liver

Figure 3:
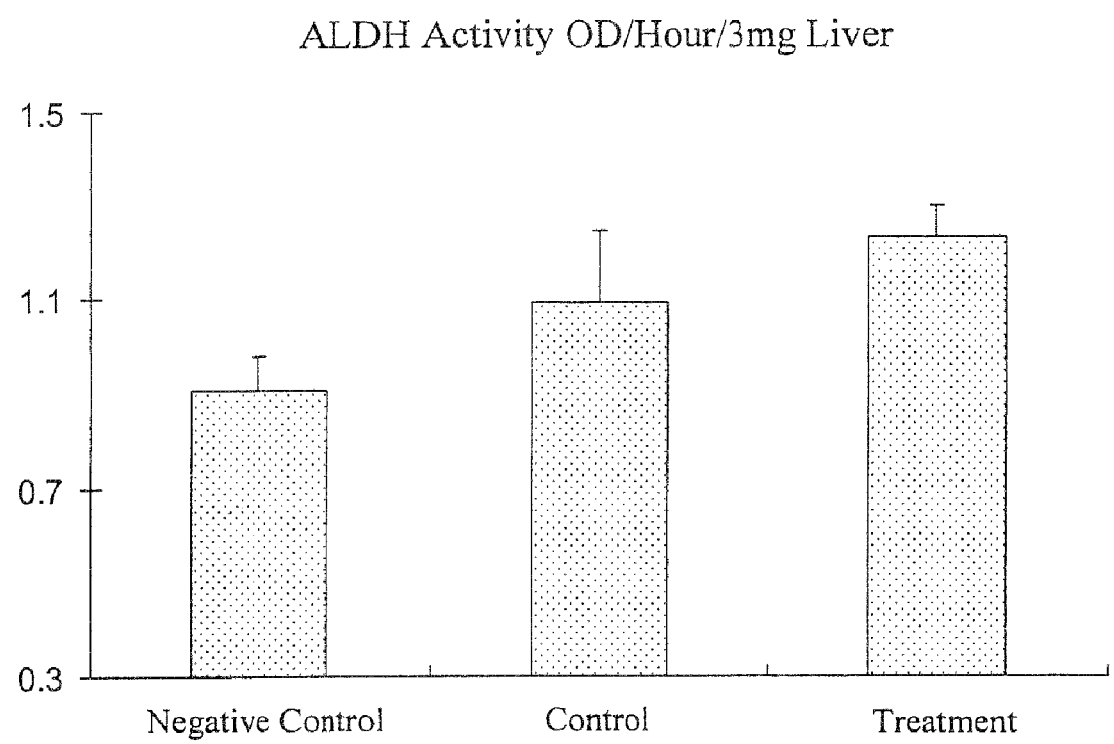
FIG. 3 shows an increase in aldehyde dehydrogenase (ALDH) activity achieved through the practice of the subject invention.

As shown in Table 3 and FIG. 3, use of CT2000 results in an increase in ALDH activity after ingestion of alcohol.

TABLE 3

|  | Negative Control | Control | Treatment |
|---|---|---|---|
| Average | 0.91 | 1.093 | 1.23 |
| SD | 0.069 | 0.15 | 0.069 |

Note:
One tail, Control vs Treatment, n = 6 per group

EXAMPLE 4

Uses, Formulations, and Administrations

Administration of the compositions of the subject invention can be accomplished by any suitable method and technique presently or prospectively known to those skilled in the art.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, compositions comprising, as an active ingredient, an effective amount of the compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, compositions of the invention will typically comprise between about 0.1% and 45%, of the total composition including carrier or diluent. The dosage used can be varied based upon the age, weight, health, or the gender of the individual to be treated.

The compositions of the invention can be used in a variety of forms, e.g., tablets, capsules, pills, powders, aerosols, granules, and oral solutions or suspensions and the like containing the indicated suitable quantities of the active ingredient. Such compositions are referred to herein generically as "pharmaceutical compositions." Typically, they can be in unit dosage form, namely, in physically discrete units suitable as unitary dosages for human consumption, each unit containing a predetermined quantity of active ingredient calculated to produce the desired therapeutic effect in association with one or more pharmaceutically acceptable other ingredients, e.g., diluent or carrier.

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:
1. A method for reducing an adverse effect caused by an elevated plasma alcohol level in a person wherein said method comprises administering, to a person who has an elevated plasma alcohol level, an effective amount of a salt of cysteamine, wherein said administration of the salt of cysteamine causes a reduction in the plasma alcohol level thereby reducing said adverse effect.

2. The method, according to claim 1, which comprises administering cysteamine hydrochloride.

3. The method, according to claim 1, wherein said adverse effects include one or more of the group consisting of headache, dehydration, congestion, stomach pains and diarrhea.

4. The method, according to claim 1, wherein said salt of cysteamine is taken orally.

5. A method for lowering the plasma ethanol concentration in a person, wherein said method comprises administering to a person who is in need of a lower plasma ethanol concentration an effective amount of a salt of cysteamine, whereby the administration of the salt of cysteamine lowers the plasma ethanol concentration.

6. The method, according to claim 5, which comprises administering cysteamine hydrochloride.

7. The method, according to claim 5, wherein said salt of cysteamine is taken orally.

8. A method for increasing acetaldehyde dehydrogenase activity in a person in need of such increase wherein said method comprises administering to the person an effective amount of a salt of cysteamine.

9. The method, according to claim 8, which comprises administering cysteamine hydrochloride.

10. A method for increasing alcohol dehydrogenase activity in a person in need of such increase wherein said method comprises administering to the person an effective amount of a salt of cysteamine.

11. The method, according to claim 10, which comprises administering cysteamine hydrochloride.

\* \* \* \* \*

UNITED STATES PATENT AND TRADEMARK OFFICE
CERTIFICATE OF CORRECTION

| | |
|---|---|
| PATENT NO. | : 8,258,187 B2 |
| APPLICATION NO. | : 12/890890 |
| DATED | : September 4, 2012 |
| INVENTOR(S) | : Wen Qin Tang et al. |

It is certified that error appears in the above-identified patent and that said Letters Patent is hereby corrected as shown below:

Column 1,
Lines 36-37, "acetic acid + $NADH^+$ + $H^+$" should read --acetic acid + NADH + $H^+$--

Signed and Sealed this
Eighteenth Day of December, 2012

David J. Kappos
*Director of the United States Patent and Trademark Office*